United States Patent
Ho

(10) Patent No.: US 11,033,274 B2
(45) Date of Patent: Jun. 15, 2021

(54) METHOD AND DEVICE FOR RESTRICTING BLOOD FLOW

(71) Applicant: MacKay Memorial Hospital, Taipei (TW)

(72) Inventor: Kung-Chen Ho, Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 757 days.

(21) Appl. No.: 14/913,358

(22) PCT Filed: Aug. 20, 2013

(86) PCT No.: PCT/CN2013/081843
§ 371 (c)(1),
(2) Date: Feb. 20, 2016

(87) PCT Pub. No.: WO2015/024181
PCT Pub. Date: Feb. 26, 2015

(65) Prior Publication Data
US 2016/0206318 A1    Jul. 21, 2016

(51) Int. Cl.
*A61B 17/12* (2006.01)
*A61B 17/132* (2006.01)

(52) U.S. Cl.
CPC .. *A61B 17/12013* (2013.01); *A61B 17/12009* (2013.01); *A61B 17/1322* (2013.01);
(Continued)

(58) Field of Classification Search
CPC .............. A61B 17/12009; A61B 17/12; A61B 2017/12004; A61B 2017/12018;
(Continued)

(56) References Cited

U.S. PATENT DOCUMENTS

| 268,407 A | * | 12/1882 | Hughes | ................ A61B 17/132 24/115 H |
| 1,704,871 A | * | 3/1929 | Salley | ................ A61B 17/1327 606/203 |

(Continued)

*Primary Examiner* — Darwin P Erezo
*Assistant Examiner* — Erin L Colello

(57) ABSTRACT

Disclosed herein are methods and devices forrestricting the blood flow of an area in a subject. The device includes a restrictor, a bolt and a strip. The restrictor includes a cylindrical body having one open end, one closed end, and a passage therethrough, in which the inner surface of the cylindrical body towards the open end is threaded; and a protrusion disposed on the outer surface of the closed end of the body. The strip is preferably made of an elastic material and is coupled to the protrusion of the restrictor at one end, while allowing the other end (i.e., the free end) to circumvent the area before passing through the passage of the cylindrical body to form a loop that can be tightened to restrict the blood flow of the area in the subject. The bolt has a head and a threaded shaft, wherein the bolt is capable of being driven into the cylindrical body through the open end to engage the threaded shaft of the bolt with the threaded inner surface of the cylindrical body until the end of the threaded shaft of the bolt is held against the strip so as to hold the loop in place and thereby restricting the blood flow of the area.

5 Claims, 5 Drawing Sheets

(52) U.S. Cl.
CPC . *A61B 17/1327* (2013.01); *A61B 2017/12004* (2013.01); *A61B 2017/12018* (2013.01)

(58) Field of Classification Search
CPC ............ A61B 17/12013; A61B 17/132; A61B 17/1322; A61B 17/1325; A61B 17/1327; A61B 17/122; A61B 177/32056; A61B 17/221; A61B 2017/2212; Y10S 403/14; Y10S 403/09; Y10S 411/917; Y10T 24/1498; Y10T 24/141; Y10T 24/1412; Y10T 24/1416; Y10T 24/142; Y10T 24/1441; Y10T 24/1443; Y10T 24/1406; F16B 2021/14; F16B 37/0864; F16B 2/08; F16B 2/065; F16L 3/233; F16L 3/2332; F16L 3/2336; F16L 3/2338; F16L 3/2334; F16L 3/137; F16L 33/085; F16L 33/10; F16L 3/12
See application file for complete search history.

(56) References Cited

U.S. PATENT DOCUMENTS

| | | | | |
|---|---|---|---|---|
| 3,465,992 A * | 9/1969 | Schuplin | ................ | F16L 3/233 248/71 |
| 4,455,715 A * | 6/1984 | Matsui | .................... | F16L 3/233 24/16 PB |
| 4,588,218 A * | 5/1986 | Guiler | ................... | G09F 3/0311 24/16 PB |
| 4,664,469 A * | 5/1987 | Sachs | ................... | H01R 4/643 439/100 |
| 4,705,245 A * | 11/1987 | Osada | .................... | F16L 3/233 24/16 PB |
| 4,708,306 A * | 11/1987 | Mitomi | ..................... | F16B 2/08 24/16 PB |
| 4,944,683 A * | 7/1990 | Leonardo | ............... | H01R 4/643 24/279 |
| 4,988,355 A * | 1/1991 | Leveen | ............ | A61B 17/12009 606/151 |
| 5,417,684 A * | 5/1995 | Jackson | ........... | A61B 17/00234 606/1 |
| 5,613,973 A * | 3/1997 | Jackson | ............. | A61B 17/0218 606/1 |
| 5,810,854 A * | 9/1998 | Beach | ................ | A61B 17/0401 24/16 PB |
| 6,217,601 B1 * | 4/2001 | Chao | .................. | A61B 17/1325 606/203 |
| 6,443,403 B1 * | 9/2002 | Page | ..................... | F16L 3/1233 24/16 PB |
| 7,052,331 B2 * | 5/2006 | Maxwell | .............. | H01R 11/285 24/274 R |
| 8,028,962 B2 * | 10/2011 | Geiger | ................. | F16L 3/2332 174/656 |
| 8,313,498 B2 * | 11/2012 | Pantages | ........... | A61B 17/0057 606/148 |
| 8,899,532 B2 * | 12/2014 | Tanaka | .................. | F16B 21/086 24/16 PB |
| 9,511,544 B2 * | 12/2016 | Hemingway | .......... | B33Y 70/00 |
| 9,869,338 B2 * | 1/2018 | Smith | .................... | F16B 35/00 |
| 2017/0107032 A1 * | 4/2017 | Smith | ................ | B65D 63/1027 |

* cited by examiner

120

110

140

METHOD AND DEVICE FOR RESTRICTING BLOOD FLOW

FIELD OF THE INVENTION

The present disclosure relates in general, to the field of medical device. More particularly, the present disclosure relates to method, assembly and/or device for restricting the blood flow of an area in a subject, such as a human.

BACKGROUND OF THE INVENTION

Bleeding control is always a primal task in any surgical procedure, and various hemostasis processes have been developed for such purpose; among them, the Pringle manoeuvreis the most commonly adopted procedure used in abdominal operations, such as hepatoectomy. In general, the portal triad is clamped by a haemostate thereby interrupting the flow of blood through the—hepatic artery—and the portal vein. Further, to prevent liver from long term ischemic, the liver needs to be re-perfused with blood be releasing the haemostate from time to time. However, repeatedly clamping and/or releasing the blood vessel during a surgical procedure is not only labor intensive, but also time-consuming, for each time the portal triad needs to be re-located before being clamped by the haemostate.

Conventional surgical procedures are mostly replaced by the laparoscopic surgery as it offers relatively smaller wound, lower risk of infection, and shorter recovery time over that of the conventional surgical procedure. Further, compared to conventional surgery, laparoscopic surgery allows the physician a better view within the abdominal cavity, with fewer blind spots, such as in the right posterior lobe and in deep left lobe. However, an additional incision in the abdominal cavity is needed for inserting relevant equipments and/or camera therein so that the laparoscopic surgery may take place.

In view of the above, if a conventional Pringle manoeuvre is to be conducted in an abdominal surgery using laparoscope, then an additional incision in the abdomen of the patient is required for introducing the haemostate therein; further, the Pringle manoeuvre would be limited due to the limited working space conferred by the laparoscopic surgery. In addition, repeatedly clamping and/or releasing the blood vessel during the entire surgical procedure is labor-intensive, as well as time-consuming.

In view of the foregoing, there exists in this art a need of an improved method and/or device for restricting blood flow in an area of a subject during an abdominal laparoscopic surgery.

SUMMARY OF THE INVENTION

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In accordance with one aspect of the present disclosure, a device for restricting the blood flow of an area in a subject is provided. The device includes a restrictor, a bolt and a strip. The restrictor includes a cylindrical body having one open end, one closed end, and a passage therethrough, in which the inner surface of the cylindrical body towards the open end is threaded; and a protrusion disposed on the outer surface of the closed end of the cylindrical body. The strip is preferably made of elastic material and is coupled to the protrusion of the restrictor at one end, while allowing the other end (i.e., the free end) to circumvent the area before passing through the passage of the cylindrical body to form a loop that can be tightened to restrict the blood flow of the area in the subject. The bolt has a head and a threaded shaft, wherein the bolt is capable of being driven into the cylindrical body through the open end to engage the threaded shaft of the bolt with the threaded inner surface of the cylindrical body until the end of the threaded shaft of the bolt is held against the strip so as to hold the loop in place and thereby restricting the blood flow of the area.

According to one embodiment of the present disclosure, the protrusion disposed at the outer surface of the closed end of the cylindrical body of the restrictor is partially threaded. In such cases, the device further includes a nut for engaging the partially threaded protrusion of the restrictor after allowing the free end of the strip to pass therethrough. According to one specific embodiment, the restrictor that includes the cylindrical body and the protrusion is formed as an integral article.

According to another embodiment of the present disclosure, the device further includes a nut, for engaging the partially threaded protrusion of the restrictor, so as to secure the coupling between the strip and the protrusion of the restrictor.

It is another aspect of the present invention to provide a medical assembly, which includes a restrictor; and a bolt; and is suitable for use with a strip to form the blood-restricting device described above for restricting the blood flow of an area in a subject. The restrictor is composed of a cylindrical body having one open end, one closed end, and a passage therethrough, in which the inner surface of the cylindrical body toward the open end is threaded; and a protrusion disposed on the outer surface of the closed end of the cylindrical body. The bolt has a head and a threaded shaft, wherein the bolt can be driven into the cylindrical body through the open end so that the threaded shaft of the bolt is engaged with the threaded inner surface of the cylindrical body of the restrictor to hold a tightened loop formed by the strip in place for restricting the blood flow of the area in the subject; in which the loop is formed by coupling one end of the strip to the protrusion, while allowing the other end to pass through the passage of the cylindrical body and leaving enough segment of the strip to circumvent the area.

In some examples, the protrusion disposed at the outer surface of the closed end of the cylindrical body of the restrictor is partially threaded. In such cases, the medical assembly further includes a nut for engaging the partially threaded protrusion of the restrictor. According to one specific embodiment, the restrictor that includes the cylindrical body and the protrusion is formed as an integral article.

It is a further aspect of the present disclosure to provide a method for restricting the blood flow of an area in a subject using the medical assembly of the present invention and a strip. The method includes steps of: coupling one end of the strip to the protrusion of the restrictor of the medical assembly of this invention; forming a loop to restrict the blood flow of the area by pulling the strip to circumvent the area and then continue to pass the free end of the strip through the passage of the cylindrical body of the restrictor; and engaging the threaded shaft of the bolt with the threaded inner surface of the cylindrical body of the restrictor so as to hold the loop in place and thereby restricting the blood flow of the area.

According to optional embodiments of this invention, the method further includes the step of, passing the free end of the strip to a nut; and engaging the nut to the protrusion of the restrictor; prior to forming the loop to restrict the blood flow of the area in the subject.

According to some embodiments of this invention, the area in the subject may be an organ or a blood vessel.

This summary is provided to introduce a selection of concepts in a simplified form that are further described below in the detail description. This summary is not intended to identify key features or essential features of the claimed subject matter, nor is it intended as an aid in determining the scope of the claimed subject matter.

The details of one or more embodiments of this disclosure are set forth in the accompanying description below. Other features and advantages of the invention will be apparent from the detail descriptions, and from claims.

BRIEF DESCRIPTION OF DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF THE INVENTION

The detailed description provided below in connection with the appended drawings is intended as a description of the present disclosure and is not intended to represent the only forms in which the present disclosure may be constructed or utilized. The description sets forth the functions of the example and the sequence of steps for constructing and operating the example. However, the same or equivalent functions and sequences may be accomplished by different examples.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Unless defined otherwise, all technical and scientific terms used herein have the same meaning as commonly understood by one of the ordinary skill in the art to which this invention belongs. The singular forms "a", "and", and "the" are used herein to include plural referents unless the context clearly dictates otherwise.

One objective of the present disclosure is to provide an assembly suitable for use in a medical procedure, particularly in laparoscopic Pringle manoeuvre for restricting blood flow of an area in a subject. Not only does the assembly of the present disclosure eliminate the labor intensive steps generally required in conventional Pringle manoeuvre, it may also control the level of blood-restricting effect in according to the actual needs in the surgical operation.

Figure 1:
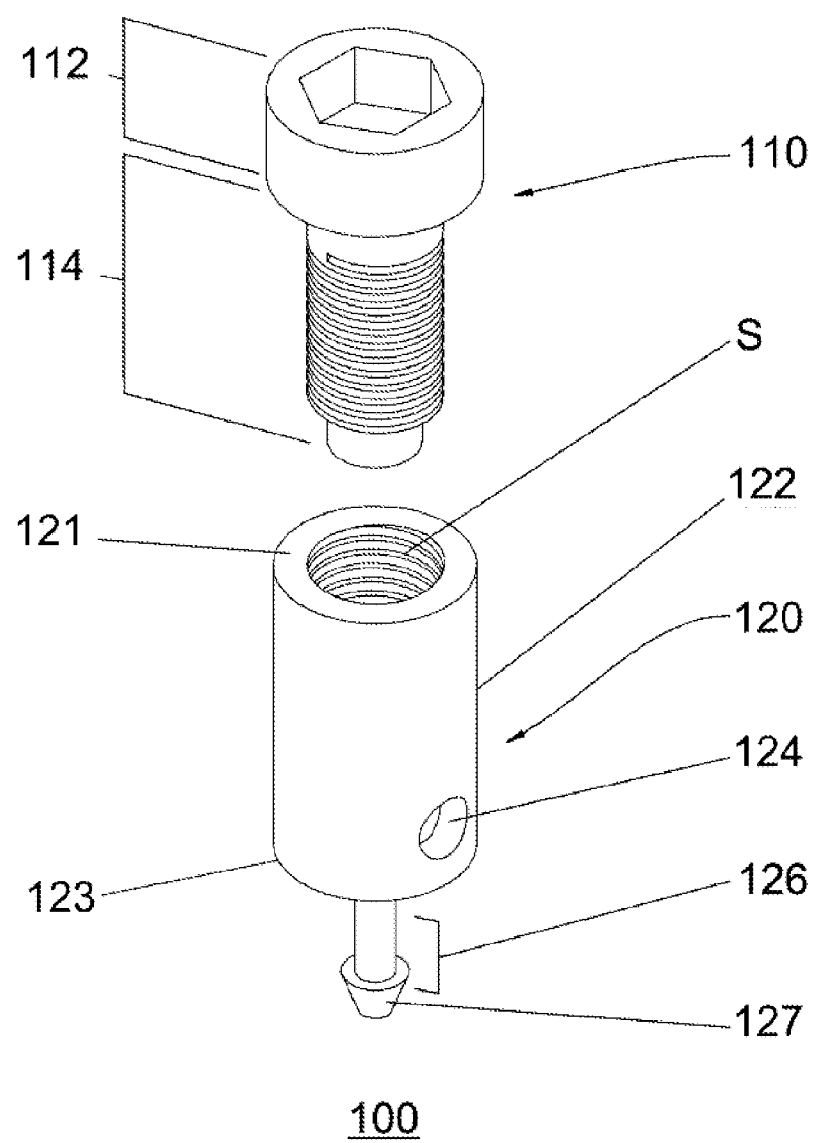
FIG. 1 is a schematic diagram illustrating a medical assembly 100 in according with one embodiment of the present disclosure.

FIG. 1 is a schematic diagram illustrating a medical assembly 100 for securing a strip to restrict the blood flow of an area in a subject. The assembly 100 comprises a bolt 110 and a restrictor 120.

Figure 2A:
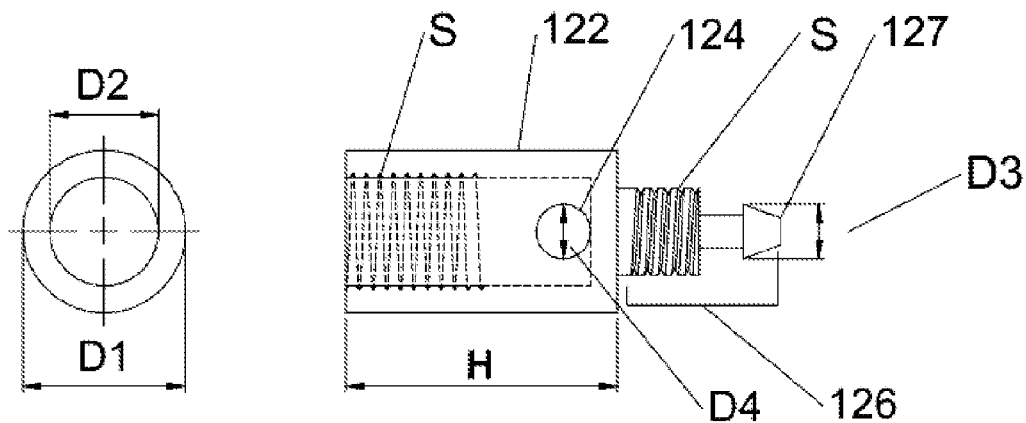
FIG. 2A is a schematic diagram illustrating the restrictor 120 of the medical assembly 100 of FIG. 1.

Referring to both FIG. 1 and FIG. 2A. As depicted in FIG. 1, the restrictor 120 is composed of a cylindrical body 122 and a protrusion 126; in which the cylindrical body 122 has an open end 121, a closed end 123, and a passage 124 disposed towards the closed end 123 of the cylindrical body 122 and laterally passes therethrough. At least part of the inner surface of the cylindrical body 122 towards the open end 121 is partially threaded (S), so as to engage with the bolt 110. As to the protrusion 126, it is disposed on the outer surface of the closed end 123 of the cylindrical body 122.

The cylindrical body 122 of the restrictor 120 has a height (H) of about 10 to 30 mm, such as about 10, 11, 12, 13, 14, 15, 16, 17, 18, 19, 20, 21, 22, 23, 24, 25, 26, 27, 28, 29 or 30 mm in height; and is preferably about 12 to 25 mm, such as about 12, 13, 14, 15, 16, 17, 18, 19, 20, 21, 22, 23, 24, or 25 mm in height; and is more preferably about 15 to 17 mm, such as about 15, 16 or 17 mm, in height. Further, the cylindrical body 122 of the restrictor 120 has an outer diameter D1 and an inner diameter D2, in which the outer diameter D1 is preferably about 8 to 25 mm, such as about 8, 9, 10, 11, 12, 13, 14, 15, 16, 17, 18, 19, 20, 21, 22, 23, 24, or 25 mm; and more preferably is about 10 to 20 mm, such as about 10, 11, 12, 13, 14, 15, 16, 17, 18, 19, or 20 mm; and most preferably is about 11 to 13 mm, such as about 11, 12 or 13 mm; whereas the inner diameter D2 is preferably about 5 to 15 mm, such as about 5, 6, 7, 8, 9, 10, 11, 12, 13, 14, or 15 mm; and more preferably is about 5 to 10 mm, such as about 5, 6, 7, 8, 9, or 10 mm; and most preferably is about 5 to 7 mm, such as about 5, 6 or 7 mm.

The protrusion 126 has an upper end and a lower end, in which the lower end is tapered into a connecting head 127 for connecting with a strip to restrict the blood flow; whereas the upper end (i.e., the end towards the closed end of the cylindrical body 122 may be optionally threaded. For example, the outer surface of the tapered connecting head 127 may be optionally corrugated to increase the friction between the strip and the head so as to secure the connection between the strip and the connection head 127. Further, the tapered connecting head 127 at its widest part has a width D3 that is about 2 to 8 mm, such as about 2, 3, 4, 5, 6, 7 or 8 mm; preferably is about 3 to 6 mm, such as about 3, 4, 5 or 6 mm; and most preferably is about 4 or 5 mm. The passage 124 is disposed towards the closed end 123 of the cylindrical body 122 to allow the strip to laterally pass therethrough. The passage 124 has an inner diameter (D4) of about 3 to 10 mm, such as about 3, 4, 5, 6, 7, 8, 9 or 10 mm; more preferably is about 3 to 8 mm, such as 3, 4, 5, 6, 7 or 8 mm; and most preferably is about 4 to 6 mm, such as 4, 5, or 6 mm.

Figure 2B:
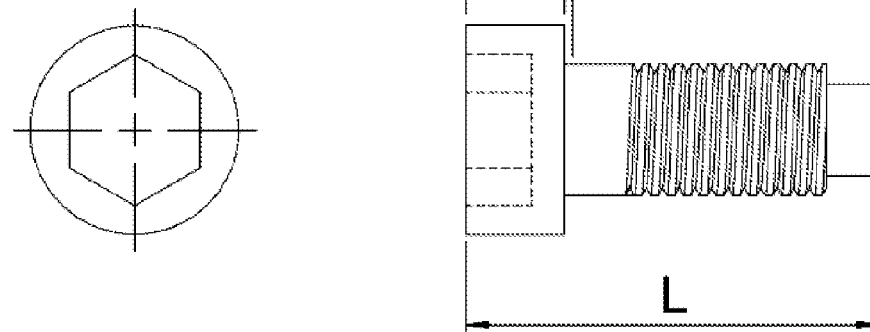
FIG. 2B is a schematic diagram illustrating the bolt 110 of the medical assembly 100 of FIG. 1.

Referring to both FIG. 1 and FIG. 2B. The bolt 110 has a head 112 and a threaded shaft 114, for engaging the cylindrical body 122 of the restrictor 120. The head 112 may further include grooves or structures that match the shape of the tool for driving the bolt 110 into the cylindrical body 122 of the restrictor 120. For example, the head 112 may have a trench that is shaped as a slot, a cross, a square or a hexagon, thereby allows the head to be driven by a tool (e.g., a wrench) with matching shape to the trench. Upon being driven into the cylindrical body 122 of the restrictor 120, the flatten end of the threaded shaft 114 of the bolt 110 is held against the strip and thus may hold the strip that passes through the passage 124 of the cylindrical body 122 in place. The bolt 110 has a length (L) of about 15 to 40 mm, such as about 15, 16, 17, 18, 19, 20, 21, 22, 23, 24, 25, 26, 27, 28, 29, 30, 31, 32, 33, 34, 35, 36, 37, 38, 39, or 40 mm; more preferably is about 18 to 25 mm, such as about 18, 19, 20, 21, 22, 23, 24, or 25 mm; and most preferably is about 19 to 21 mm, such as about 19, 20 or 21 mm. In one example, the restrictor 120 of the medical assembly 100 that consists of the cylindrical body 122 and the protrusion 126 is an integral article.

It is a further aspect of the present disclosure to provide a blood-restricting device suitable for use with Pringle manoeuvre during a surgical procedure. Compared with the conventional device, the blood-restricting device of the present disclosure is easier to operate, quick acting, hence may aid in simplifying the steps necessary for restricting blood flow during a medical procedure. Further, the blood-restricting device of the present disclosure allows the physician to adjust the blood flow in a particular area in a more timely fusion. Another advantage of the present blood-restricting device is that it is compact in size, and works well with the laparoscope, hence further eliminates the need of having an additional incision made in the abdomen of the subject for introducing the operating apparatus into the body, which in turn enhances the efficiency of the surgical procedure, and reduces the pain felt by the subject.

Figure 3:
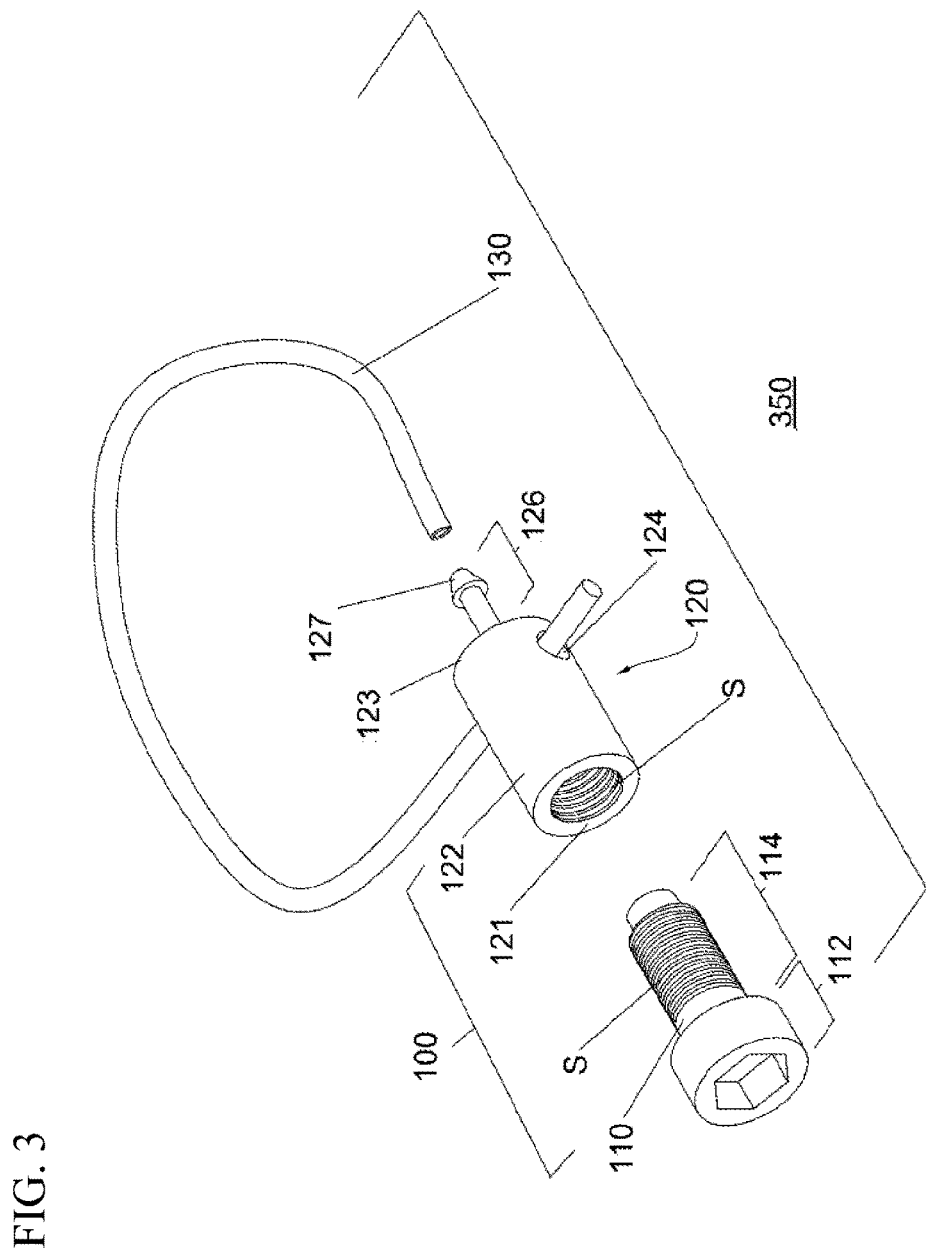
FIG. 3 is a schematic diagram illustrating the blood-restricting device 350 in according with one embodiment of the present disclosure.

FIG. 3 is a schematic diagram illustrating the blood-restricting device 350 in according to one embodiment of the present invention. As depicted in FIG. 3, in addition to the medical assembly 100 described above, the blood-restricting device 350 further includes a strip 130. In general, the restrictor 120 and the bolt 110 of the blood-restricting device 350 are same as those in FIG. 1; hence these components are not discussed herein for the purpose of brevity. The strip 130 is coupled to the protrusion 126 of the cylindrical body 122 at one end, while allowing the free end of the strip 130 to pass through the passage 124 of the cylindrical body 122 and thereby forming a loop for restricting the blood flow of an area of interest. The length of the strip 130 may be adjusted according to the actual need determined by the physician that performs the surgery. In general, the strip 130 may has a length of about 5 to 20 cm, such as about 5、6、7、8、9、10、11、12、13、14、15、16、17、18、19 or 20; preferably about 8 to 16 cm, such as 8、9、10、11、12、13、14、15 or 16; and more preferably about 10 to 15 cm, such as 10、11、12、13、14 or 15. According to an optional example, the strip 130 may be made of elastic material, and may be in the form of a tube. For example, the strip 130 is made of one or more medical thermoplastic materials, including, but not limiting to siliceous material, polypropylene or polyvinyl chloride.

Referring again to FIG. 3, the blood-restricting device 350 of the present invention is assembled in accordance with steps described as follows. One end of the strip 130 is coupled to the protrusion 126 of the restrictor 120 by tightly engaging with the connecting head 127. Then, another end (i.e., the free end) of the strip 130 is passed through the passage 124 of the restrictor 120 thereby forming a loop, which may be tightened to restrict the blood flow of an area of interest. The bolt 110 is then driven into the cylindrical body 122 of the restrictor 120 until the flatten end of the shaft 114 of the bolt 110 is held against the strip 130 retained within the passage 124, thereby holding the loop formed by the strip 130 in place. Further, the size of the loop may be adjusted by steps of: loosening the bolt 110, adjusting the length of the loop in according to the actual need, then tightening the bolt 110 again.

Figure 4:
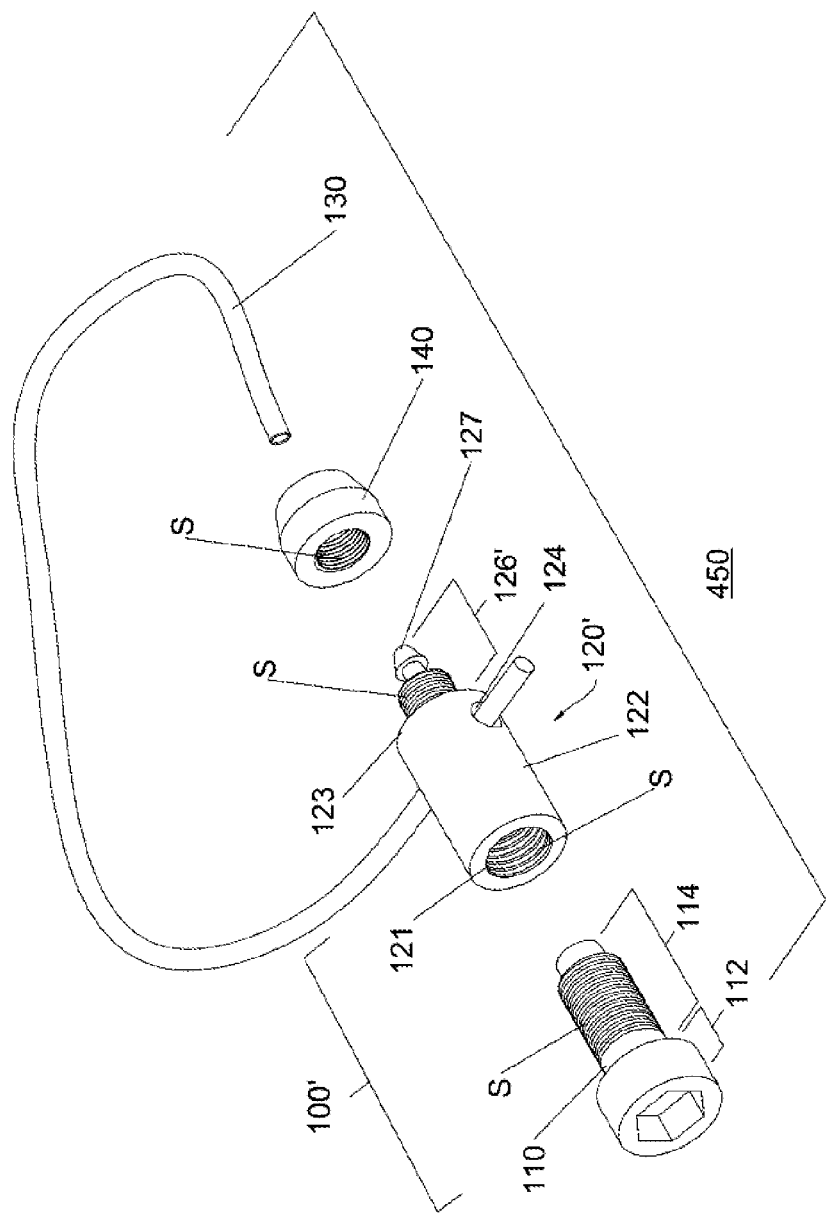
FIG. 4 is a schematic diagram illustrating the blood-restricting device 450 in according with another embodiment of the present disclosure.

FIG. 4 is a schematic diagram illustrating the blood-restricting device 450 in accordance with another embodiment of the present invention. In this embodiment, the arrangement of the components of the device 450 is relatively the same as that in FIG. 3, comprising a medical assembly 100', a tube 130 and a nut 140 to ensure a secure connection between the strip and the restrictor. Further, the restrictor 120' in this embodiment differs from the restrictor 120 of FIG. 1 in that the upper end of the protrusion 126' is threaded (S), and the lower end of the protrusion 126' is tapered into a connecting head 127.

Figure 5:
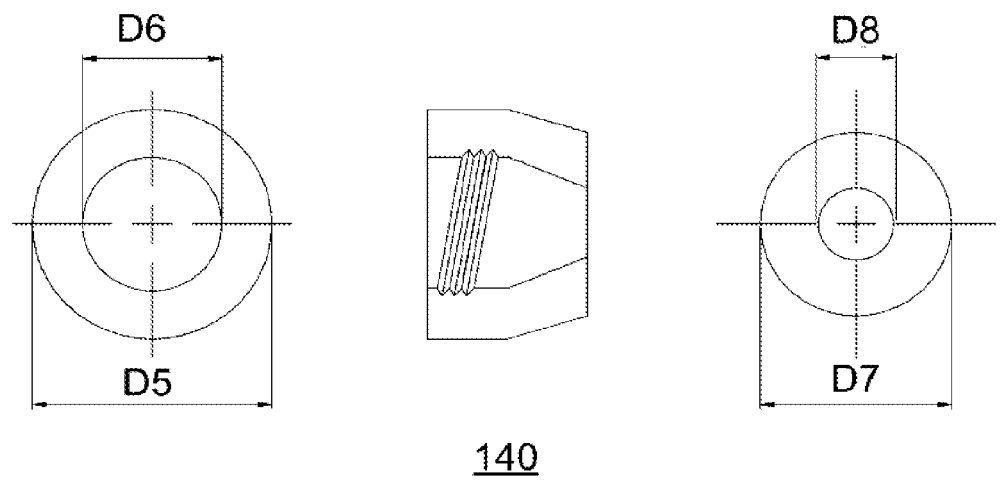
FIG. 5 is a schematic diagram illustrating the nut 140 of the blood-restricting device 450 of FIG. 4.

Please refer to FIG. 5, in which the nut 140 suitable for used in this embodiment is depicted. The inner surface of the nut 140 is partially threaded (S), so as to match with the threaded upper end of the protrusion 126'. According to one example of this embodiment, the nut 140 should be roomy enough to allow the strip 130 to pass through while it is tightly engaged with the protrusion 126' of the restrictor 120'. The upper end of the nut 140 has an outer diameter D5 and an inner diameter D6; in which D5 is preferably about 6 to 20 mm, such as about 6, 7, 8, 9, 10, 11, 12, 13, 14, 15, 16, 17, 18, 19, or 20 mm; more preferably about 8 to 15 mm, such as about 8, 9, 10, 11, 12, 13, 14, or 15 mm; and most preferably about 9 to 12 mm, such as 9, 10, 11 or 12 mm; whereas D6 is preferably about 4 to 11 mm, such as about 4, 5, 6, 7, 8, 9, 10, or 11 mm; more preferably about 6 to 9 mm, such as about 6, 7, 8 or 9 mm; and most preferably about 7 or 8 mm. The lower end of the nut 140 also has an outer diameter D7 and an inner diameter D8; in which D7 is preferably about 5 to 14 mm, such as about 5, 6, 7, 8, 9, 10, 11, 12, 13, or 14 mm; more preferably about 7 to 12 mm, such as about 7, 8, 9, 10, 11, or 12 mm; and most preferably about 9 or 10 mm; whereas D8 is preferably about 3 to 7 mm, such as about 3, 4, 5, 6, or 7 mm; more preferably about 4 to 6 mm, such as about 4, 5, or 6 mm; and most preferably about 5 mm.

As depicted in FIG. 4, the blood-restricting device 450 of this invention is assembled in accordance with steps as follows. First, allow the strip 130 to pass the nut 140; then connect one end of the strip 130 with the connecting head 127. After that, allow the nut 140 to be threaded onto the protrusion 126' by engaging respective threaded portions of the nut 140 and the protrusion 126'. Let the other end of the strip 130 pass through the passage 124 of the cylindrical body 122 of the restrictor 120' and forms a loop. The bolt 110 is then driven into the cylindrical body 122 of the restrictor 120' until the flatten end of the shaft of the bolt 110 is held against the strip 130 to keep the loop in place. In the case when the size of the loop needs to be re-adjusted or the device needs to be dissembled, the bolt 110 may be loosen to release the strip 130 to re-adjust its length or to be completely removed from the passage 124. In optional embodiments, the restrictor of the present invention that comprises the cylindrical body and the protrusion may be formed as an integral article.

A further aspect of the present disclosure is to provide a method of restricting the blood flow of an area in a subject. The present method may be used with laparoscope in a surgical procedure, and when compared with the conventional blood-restricting process, the method of the present invention is easy to use, quick acting, and can provide intermitting blood-restriction effect to an area of interest in a real-time manner.

Specifically, the method comprises steps of: coupling one end of a strip to the protrusion of the restrictor of the medical assembly of the present invention as described above; forming a loop to restrict the blood flow of the area by pulling the strip to surround the area of interest and then passing the free end of the strip through the passage of the cylindrical body of the restrictor; and engaging the threaded shaft of the bolt with the threaded inner surface of the cylindrical body of the restrictor so as to hold the loop in place and thereby restricting the blood flow of the area of interest. In some optional embodiments, the area of interest may be an organ, a blood vessel or a combination thereof.

Figure 6:
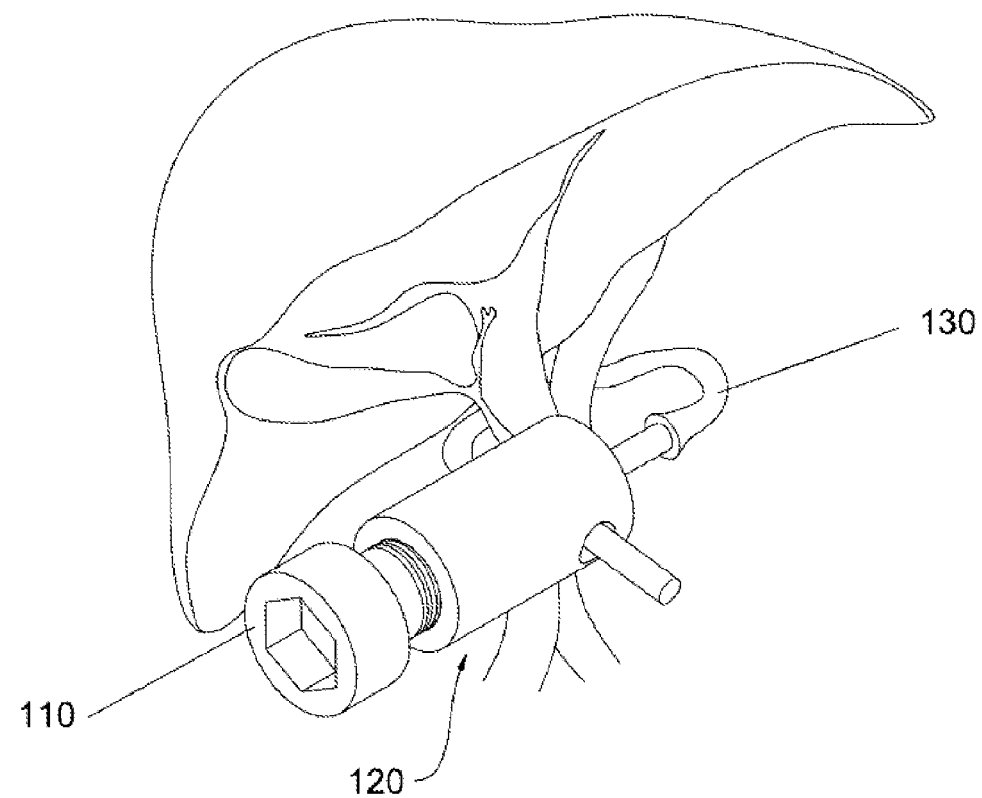
FIG. 6 is a schematic diagram illustrating the operation of the blood-restricting device 350 of FIG. 3 in according with one embodiment of the present invention.

Referring to both FIGS. 3 and 6, which illustrate the application of the blood-restricting device of the present invention in a surgical procedure, such as Pringle manoeuvre in hepatoectomy. During operation, one end of the strip 130 is coupled to the restrictor 120 by tightly engaging with the connecting head 127 of the protrusion 126. Then, allow the free end of the strip 130 to surround the portal triad before passing it into the passage 124 of the cylindrical body and thereby forms a loop. Tighten the loop so that the portal triad is strictly restricted by the strip 130. Finally, driving the bolt 110 into the cylindrical body 122 of the restrictor 120 until it is held against the strip 130 to hold the loop in place and thereby restricting the blood flow in the liver. Further, to prevent the liver from being severely damaged due to long term ischemia during the surgery, the liver needs to be re-perfused with blood from time to time, hence the bolt 110 may be loosen to release the loop formed by the strip 130 from its current holding position and re-adjust the length to enlarge the loop size. Upon completion of the blood re-perfusion, the loop size is re-adjusted so that it is tightly held against the portal triad with the aid of the bolt 110. The blood flow in the liver area may be intermittently restricted by repeatedly performing the procedure described herein until the surgery completes. It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A device for restricting the blood flow through a portal triad in a subject consisting of:
    a restrictor consisting of,
        a cylindrical body having one open end, one closed end, and a passage therethrough, in which an inner surface of the cylindrical body at the open end is threaded; and
        a protrusion disposed on an outer surface of the closed end of the cylindrical body, wherein an outer surface of the protrusion is partially threaded;
    a bolt having a head and a threaded shaft;
    a strip in a tube form having a first end which is open, a second end, a lumen therethrough, wherein the outer surface of the protrusion of the restrictor is inserted into the lumen via the first end of the strip to form a connection between the strip and the protrusion, and the second end of the strip is configured to circumvent the portal triad in the subject before being passed through the passage of the cylindrical body, so that the strip forms a loop that is configured to be tightened to restrict the blood flow of the portal triad in the subject; and
    a nut for engaging the protrusion of the restrictor, wherein the nut is configured to secure the connection between the strip and the protrusion of the restrictor;
    wherein the bolt is configured to be driven into the cylindrical body through the open end of the cylindrical body until the end of the threaded shaft of the bolt is held against the strip, thereby holding the loop in place and restricting the blood flow through portal triad in the subject.

2. The device of claim 1, wherein the cylindrical body and the protrusion are formed into an integral article.

3. The device of claim 1, wherein the strip is made of an elastic material.

4. A method of restricting the blood flow through a portal triad in a subject using a device of claim 1, comprising,
    coupling the first end of the strip to the protrusion of the restrictor of the device;
        pulling the strip to circumvent the portal triad until the second end of the strip passes through the passage of the cylindrical body of the restrictor, thereby forming the loop that is configured to restrict the blood flow through the portal triad; and
        driving the bolt into the cylindrical body through the open end to engage the threaded shaft of the bolt with the inner surface of the cylindrical body until the end of the threaded shaft of the bolt is held against the strip, thereby holding the loop in place and restricting the blood flow through the portal triad.

5. The method of claim 4, further comprising passing the second end of the strip through the nut; and engaging the nut to the protrusion of the restrictor prior to forming the loop.

* * * * *